(12) United States Patent
Homann

(10) Patent No.: US 6,224,855 B1
(45) Date of Patent: May 1, 2001

(54) METHOD AND DEVICE FOR TREATING NATURAL OR ARTIFICIAL PLASTIC FINGERNAILS OR TOENAILS

(76) Inventor: Steffen Homann, Auwaldstrasse 1, D-79110, Freiburg (DE)

( * ) Notice: Subject to any disclaimer, the term of this patent is extended or adjusted under 35 U.S.C. 154(b) by 0 days.

(21) Appl. No.: 09/000,047
(22) PCT Filed: Jul. 12, 1996
(86) PCT No.: PCT/EP96/03071
§ 371 Date: Jan. 15, 1998
§ 102(e) Date: Jan. 15, 1998
(87) PCT Pub. No.: WO97/03585
PCT Pub. Date: Feb. 6, 1997

(30) Foreign Application Priority Data

Jul. 15, 1995 (DE) .......... 295 11 466 U
Feb. 2, 1996 (DE) .......... 196 03 716

(51) Int. Cl.[7] .......... A61K 7/04; A45D 29/00
(52) U.S. Cl. .......... 424/61; 132/73
(58) Field of Search .......... 132/73; 424/61, 424/400; 607/111; 128/898; 315/32, 46

(56) References Cited

U.S. PATENT DOCUMENTS

| | | | |
|---|---|---|---|
| 1,566,987 | * 5/1925 | Simmons | 607/111 |
| 2,569,250 | 9/1951 | Mims | 219/29 |
| 5,782,249 | * 7/1998 | Weber et al. | 132/200 |

FOREIGN PATENT DOCUMENTS

| | | |
|---|---|---|
| 1557314 | 2/1970 | (DE) . |
| 2703056 | 7/1978 | (DE) . |
| 3727916 | 3/1989 | (DE) . |
| 0031147 | 7/1981 | (EP) . |
| 0 170 482 | * 2/1986 | (EP) . |
| 0170482 | 2/1986 | (EP) . |
| 2212746 | 12/1972 | (FR) . |
| 6292683 | 4/1993 | (JP) . |
| WO 97/03583 | * 2/1997 | (WO) . |

* cited by examiner

*Primary Examiner*—Thurman K. Page
*Assistant Examiner*—S. Howard
(74) *Attorney, Agent, or Firm*—Gudrun E. Huckett Patent Agent (57) ABSTRACT

A method for treating natural fingernails and toenails and artificial fingernails and toenails includes the step of heating the fingernail or toenail to a temperature at which the material of the fingernail or toenail begins to melt. The forward edge of the nail can be fused and sealed by this method or the surface of the nail can be smoothed and polished. The device for treating natural fingernails and toenails and artificial fingernails and toenails has a heating unit for heating the fingernail or toenail.

14 Claims, 8 Drawing Sheets

METHOD AND DEVICE FOR TREATING NATURAL OR ARTIFICIAL PLASTIC FINGERNAILS OR TOENAILS

BACKGROUND OF THE INVENTION

The invention relates to a method and device for treating natural or artificial, plastic fingernails or toenails.

The inventive method as well as the corresponding device for treating fingernails and toenails is used primarily in the cosmetic field for manicure as well as pedicure. The conventional treatment of fingernails and toenails is such that they are only cut and, if necessary, filed. It is a disadvantage that the nails are often brittle and rip, resulting in the associated nail problems. The result is that due to the jagged forward nail edge the nails are caught on fabrics and in extreme cases will pull threads. Also, ripped and brittle nails give an ungroomed appearance. In addition to the treatment of natural fingernails (as well as toenails) the inventive method can also be used for treating artificial fingernails which are comprised of plastic. Here, similar problems as with natural fingernails occur. For example, the artificial fingernails easily rip or are damaged otherwise so that they can no longer be usable.

The invention has as an object to provide a method as well as a device for treating natural or artificial, plastic fingernails or toenails.

SUMMARY OF THE INVENTION

As a technical solution it is inventively suggested that the nail is heated in portions to such a temperature that the nail substance at the desired location will melt to some extent.

Such a heat treatment of a fingernail (natural or artificial) or of a toenail has the advantage that the condition as well as the outer appearance of the nail in comparison to untreated nails can be considerably improved by technically simple means. The inventive idea is that the nail is heated to such a temperature that it partly melts, thus achieving the desired effect. It is not necessary to heat the nail across its entire extension but only in such area or areas in which the melting effect is needed. Which temperature is to be applied depends on the respective application. This holds true especially for artificial fingernails made of plastic. Here, the temperature depends on the nature of the plastic material.

A first field of application of the inventive heat treatment of a nail is to heat the leading edge of the nail. This application is especially suitable for natural fingernails and toenails whereby it is advantageous that the keratin material at the forward nail end is partly melted and fused by heating and thereby sealed. The nail thus can no longer rip and no longer becomes brittle. Melting of the keratin material also results in a smooth surface at the forward nail edge so that no points of attack for catching etc. on a fabric are present. Finally, the forward nail edge is reinforced and stabilized. Of course, it is also possible to heat the forward nail edges of artificial fingernails in order to prevent ripping.

A further application is suggested in that the surface of the nails are polished by heat application. In general, the nail surface is polished by rubbing a respective polishing medium onto the nail surface. With the inventive additional heat application, the surface of the nail can be polished in an improved manner whereby the temperature is approximately between 40° C. and 150° C. The nail surface receives improved shine as well as an improved shape by applying the temperature.

In a further embodiment, an additional polishing medium can be used for polishing in order to improve the polishing effect. As a polishing material a cream or paste can be used. In the alternative, a polishing stone as well as polishing paper or similar material can be attached to the polishing tool.

In a further embodiment it is suggested that during polishing the cuticle is pushed back or removed. The application of heat also has a positive effect in this regard.

As mentioned before, the inventive heat treatment method is not only suitable for natural fingernails and toenails but also for artificial fingernails. A further embodiment of the inventive heat treatment method thus suggests that for artificial fingernails damaged locations are repaired by heating. The sealing and fusing of artificial fingernails prevents further ripping. Also, defective nails can be repaired or mended.

A further embodiment for artificial fingernails suggests to fuse by heating an extension piece thereto. Thus, an artificial nail is extended by fusing onto an already present artificial nail.

A further preferred embodiment suggests that an artificial fingernail is attached by heating onto a natural fingernail. Thus, an artificial nail is no longer attached by adhesives to a natural nail, but the artificial nail is directly melted or fused onto the natural nail by temperature application. The fusing process can be performed by placing the artificial fingernail onto the natural fingernail and heating subsequently the artificial fingernail from above so that the underside will partly melt. In the alternative, it is also possible to heat the underside of the artificial nail directly and to press it onto the natural fingernail subsequently. Finally, it is also possible that fusing of the artificial fingernail is carried out such that the forward nail edge of the natural nail is fused with the artificial nail at this forward nail area whereby especially a plastic material is used as a fusing material which corresponds to the artificial nail material. The artificial fingernail is thus actually fused to the forward nail area of the natural nail in the manner similar to a soldering process.

It is finally suggested with the inventive method to apply an electrical current in addition to, or alternative to, heating. This electrical current generates electrical stimulation.

As a technical solution in regard to the device for performing the method, the invention suggests a heatable device for heating the nails. With such a heatable heating device it is possible in a technically simple manner to perform the desired heat treatment.

In a first alternative it is suggested that the heatable device can be guided along the forward nail edge. The advantage of a treatment device for fingernails and toenails embodied such is that the keratin material at the forward nail end is partly melted and fused by heating and thus sealed. The nail can no longer rip and no longer becomes brittle. By fusing the keratin material, a smooth surface at the forward nail edge results so that no point of attack for catching etc. at fabric is present. While in a first alternative the nail to be treated is introduced into a correspondingly embodied heating device, in a preferred second alternative it is suggested that the heatable device is guidable along the forward nail edge. This has the advantage that the treatment device can follow any desired nail contour.

The heatable device may be rod-shaped, especially cylindrically shaped, and can be guided along the forward nail edge either with its curved mantle surface or with its end face. This provides the technically most simple embodiment for a heatable device which can be guided along the forward edge of a nail. Preferably, the curved mantle surface of the heatable device is employed for being guided along the forward nail edge. Of course, the end face of the cylinder can also be used whereby, of course, it may be profiled. It is feasible to employ, in addition to a planar end face, a convex or concave end face. Also, other curved profiled shapes are possible with which guiding along the forward nail edge is possible.

In general, it is possible that the treatment device is embodied in the form of a file or scissors. A preferred embodiment suggests, however, that the heatable device has a slot-shaped groove for receiving the forward nail edge. This slot-shaped groove for receiving the forward nail edge serves actually as a guide groove which engages the nail partially so that not only the forward end of the nail facing the end face is sealed but also neighboring top side and underside of the nail. Furthermore, the treatment device can be more easily manipulated by having this guide groove.

A further embodiment suggests that the groove is provided at the leading end face of the heatable device whereby this leading end face of the heatable device together with the groove is either planar or convex or concave. Especially by providing a curved groove, an optimal sealing of the forward nail edge is possible because the slot-shaped groove can be optimally guided along the contour of the nail edge. Depending on the shape of the curve, it is possible to perform fine or coarse treatment of the nail.

In the case that the heatable device is cylindrically shaped, it is suggested in a further embodiment to provide the groove at the periphery of the cylindrical mantle surface. This is a further embodiment of the simplest variant in which the heatable device is formed only by a cylinder. The further embodiment of this simplest variant now provides a circumferential groove for receiving the nail.

A further alternative embodiment suggests that the heatable device is moveable across the surface of the nail for polishing. This is a technically simple solution for optimizing the polishing effect. During movement of the heatable device, the surface of the nail material is lightly melted and made more uniform and this results in the polishing effect. By moving the heating device, the uniformness of the surface is further improved.

Another embodiment suggests that the heatable device is slightly curved. The curvature matches the nail contour.

In a further embodiment it is suggested that the side of the heatable device contacting the nail surface it is provided with a polishing medium coating. This may be in the form of polishing paper, a polishing stone or similar material.

A further alternative embodiment suggests that the heatable device is curved and can be pressed onto an artificial fingernail for fastening onto a natural fingernail. With this device a technically simple solution is provided in order to fasten artificial fingernails on natural fingernails. The basic idea lies in that the artificial fingernail is to be heated such that it will melt slightly at the contact surface to the natural fingernail and thus fuses the two fingernails permanently in this manner. It is also possible to heat with the heating device the underside of the artificial fingernail in order to press it onto the natural fingernail.

A first alternative of the heat supply for the treatment device is that the heatable device is a heat storage device with an external heating means in the form of a furnace. In practice this is realized such that the treatment device when not in use is positioned in the furnace where the heatable device can be maintained at the desired operating temperature. For employing the treatment device, it is then removed from the furnace and can then be used for a certain amount of time as long as the heatable device has the required minimum temperature.

In an alternative it is suggested that the heatable device has an integrated electrical resistance heating unit. The advantage of this alternative is that the desired temperature is always present and the treatment device is thus always in an optimal operating condition. However, an electrical control device with an electrical supply cable extending to the treatment device is necessary. The application of the temperature via the electrical resistance heating unit is realized with electrical heat resistors, heating foils or heating cartridges. The heating foils are preferably glued onto a base body or vulcanized thereto. Furthermore, the electrical resistance heating unit preferably comprises a temperature sensor in order to realize a corresponding temperature control.

Another embodiment suggests that the heating temperature is controllable. This includes that with the control device the desired temperature of the treatment device can be adjusted and selected which can be different from case to case. In order to control the heating temperature, a temperature sensor for controlling the actual temperature is preferably provided.

In a further embodiment it is suggested that the heatable device comprises a heating element arranged at a holder. This is to be understood such that the heating element is a separate component, especially a metal insert into a manipulating housing which is embodied as a pin-like or grip-like rod. The advantage of such a heating element body is that the entire construction of the treatment device is technically simple because the heating element must only be inserted into the holder. Also, an exchange or replacement of a defective heating element is easily possible without the holder becoming unusable.

A further development suggests that a separate heating cartridge or heating pad is arranged in the heating element. This allows use of commercial heating cartridges or heating pads which can be introduced into the special designed heating element. This results in a constructive simplification. Also, the treatment device can be inexpensively manufactured.

Finally, in another embodiment of the inventive treatment device an additional device for covering and/or cooling of the portions of the nail or the finger or toe not to be treated is suggested. This additional device has the function of an auxiliary means for improved treating of the nail. The basic idea lies in a protective finger holder which surrounds the entire finger and only exposes the tip of the nail. This protective finger holder is filled with moist thin cotton balls or a comparable material such as linen, suede, etc. This moist cotton ball serves for cooling. Of course, it is also possible to provide the cotton ball with a care product. It is also possible to provide an external holder which has an inner cushion and a cushion enclosing it, for example, made of silicone material or plastic material. A cooling liquid can be pumped through this cushion by a pump, for example, cooling water for cooling the finger or the toe. It is also possible to permanently fill the cushion with the cooling medium in a closed system.

BRIEF DESCRIPTION OF THE DRAWINGS

Further embodiments of the inventive device for treating fingernails and toenails will be disclosed in the following with the aid of the drawings.

It is shown in.

DESCRIPTION OF PREFERRED EMBODIMENTS

Figure 1:
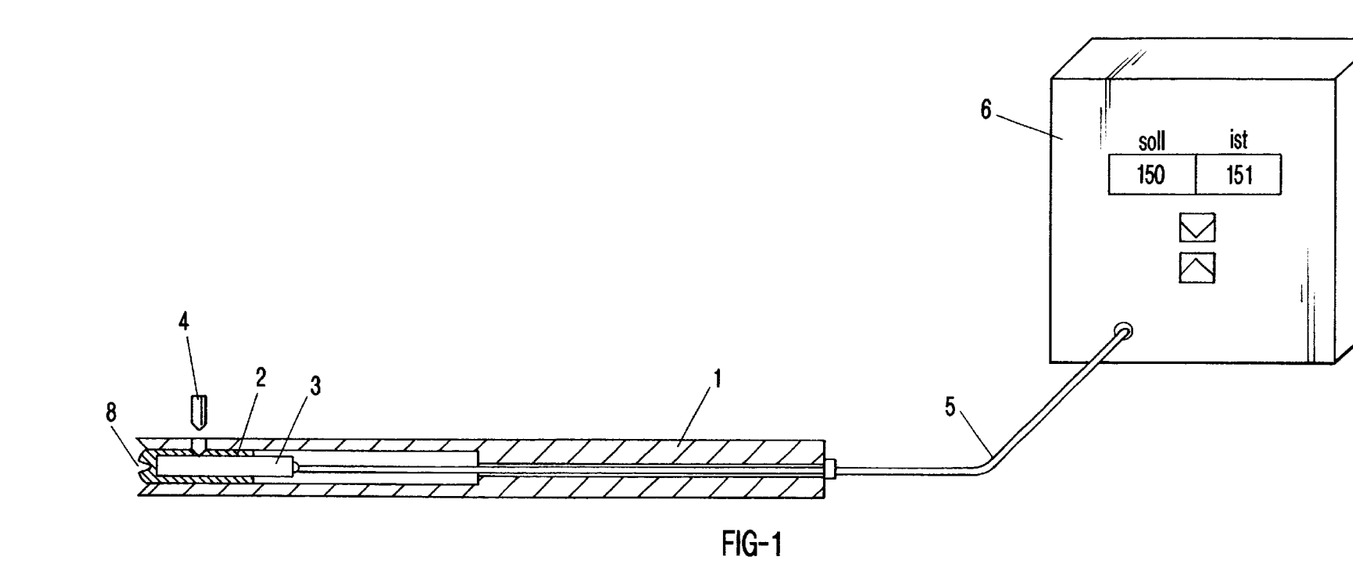
FIG. 1 a schematic sectional view of the first embodiment of the device for treating the forward nail edge of fingernails and toenails.

FIG. 1 shows a first version of a device for treating fingernails and toenails. A pin-shaped and tubular holder 1 is provided. In an opening at the end face a cylindrical heating element 2 is located. It is provided with a type of blind bore in which a heating cartridge 3 is arranged. The heating element 2 is secured in the holder 1 by a set screw 4. The commercially available heating cartridge 3 comprises at its back side a cable 5 which is guided through the rear tubular open end of the rod-shaped holder 1 and connected to a control unit 6 which, on the one hand, supplies the heating cartridge 3 with current for heating, and on the other hand, maintains the heating temperature at a constant value. First of all, however, the heating element 2 has a groove 8 at its forward end face that extends across the diameter of the end face 7.

Figure 3A:
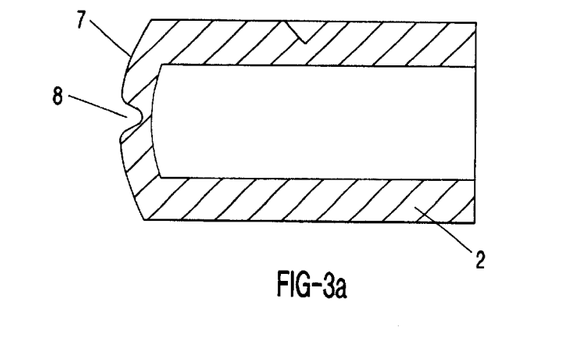
FIGS. 3a and b a first embodiment of a heating element with convex end face in different views.
Figure 3B:
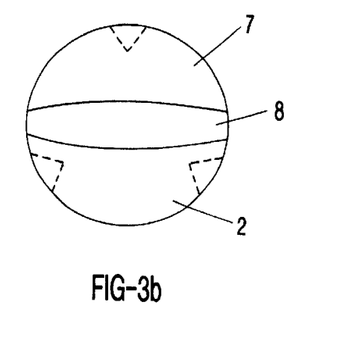
Figure 4A:
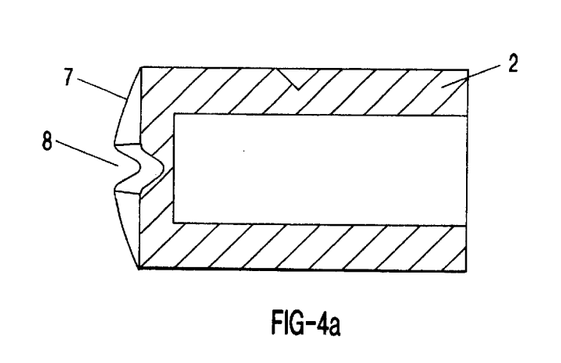
FIGS. 4a–4c a second embodiment of the heating element with a concave end face in different views.
Figure 4B:
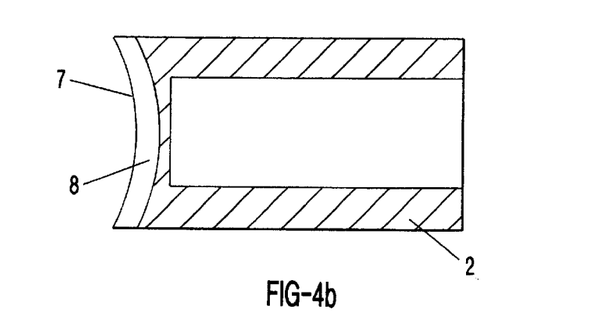
Figure 4C:
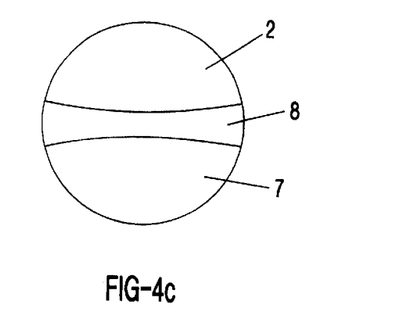

In FIGS. 3a and b as well as FIGS. 4a to c different embodiments of the heating element 2 are represented with differently embodied grooves 8. In the first embodiment represented in FIGS. 3a and b the end face 7 of the heating element 2 is convexly curved as can be seen especially in the sectional view of FIG. 3a. FIG. 3b shows that the slot-shaped groove 8 extends over the entire diameter of the cylindrical heating element 2. The heating element 2 in the embodiment of FIGS. 4a to c has a concavely embodied end face 7 as can be especially seen in the two sectional views of FIGS. 4a and b, whereby FIG. 4b shows a longitudinal section perpendicularly to the one shown in FIG. 4a. In FIG. 4c it can be seen that the slot-shaped groove 8 extends over the entire diameter of the end face 7.

The thus embodied treatment device for fingernails and toenails functions as follows:

With the control device 6 the heating element 2 is heated to a preset, predetermined temperature. The operator can guide the device with the grip-shaped holder 1 along the forward edge of the nail whereby the forward edge of the nail is received in the groove 8. The heating effect on the nail melts some of the keratin material and thus seals the forward nail edge.

Figure 2:
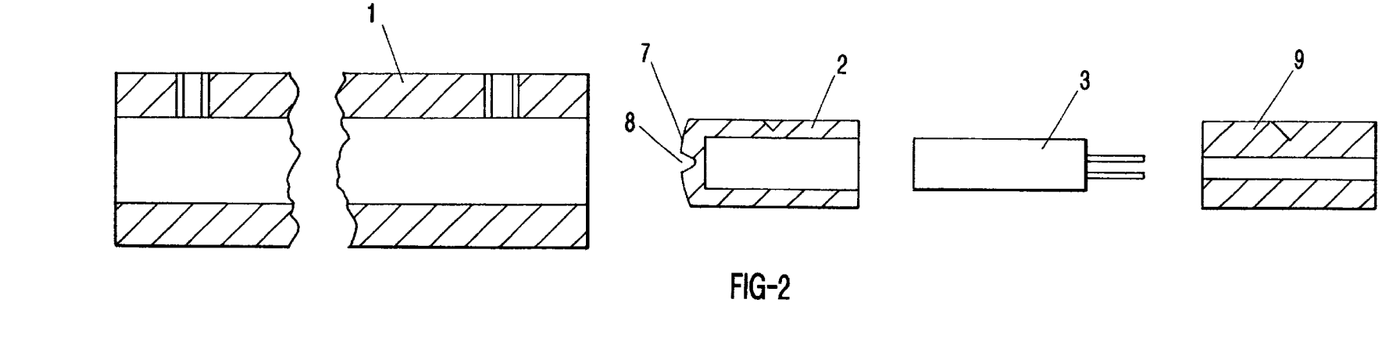
FIG. 2 an embodiment modified relative to FIG. 1 in an exploded view.

In FIG. 2 an embodiment modified relative to FIG. 1 of the treatment device is represented in an exploded view. All of the details, i.e., the holder 1, the heating element 2, as well as the heating cartridge 3 can be seen better. The only difference to the embodiment of FIG. 1 is that the embodiment of FIG. 2, instead of the massive rear tubular end of the holder 1, has a separate insert 9 which can be inserted into the tubular holder 1 and can be secured thereat, for example, by a set screw.

Figure 9A:
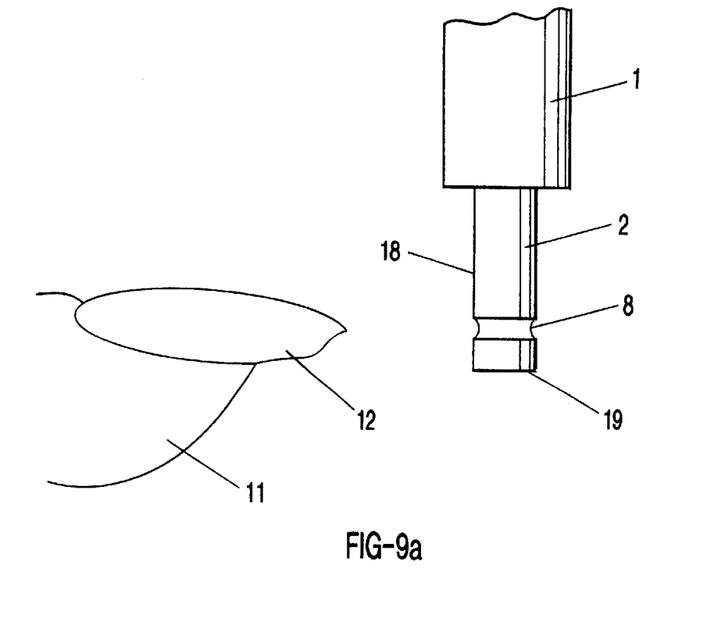
FIGS. 9a and b a third embodiment of the treatment device in which the heatable device is cylindrical and comprises an annular circumferential groove.
Figure 9B:
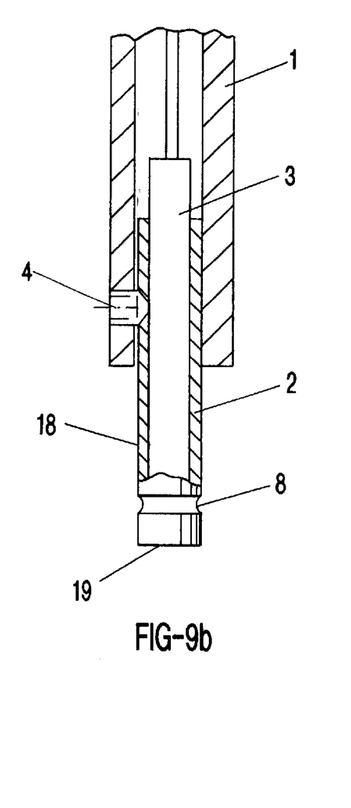

FIGS. 9a and b show a side view as well as a sectional view of a third embodiment of the treatment device. An elongate holder 1 is also present in this embodiment. In the opening at the end face a cylindrical heating element 2 is provided in which a heating cartridge 3 is arranged. As can be seen in the drawing, the forward end of the cylindrically shaped heating element 2 projects past the end face of the holder 1. Furthermore, the cylindrical heating element 2, in the area of the forward end, has a circumferential groove 8. This groove 8 receives the forward nail edge of a fingernail 12, as can be seen especially well in FIG. 9a.

Figure 10:
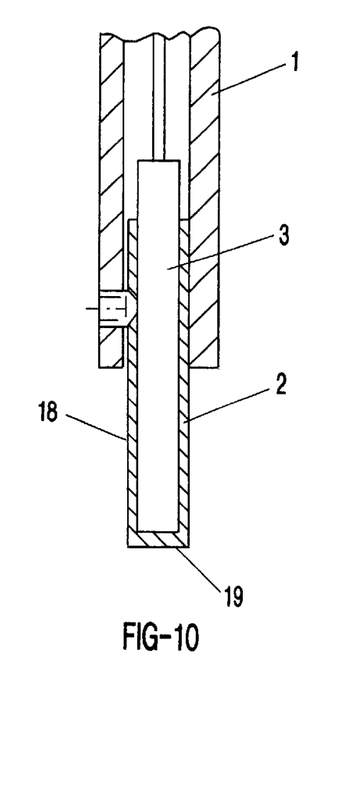
FIG. 10 a fourth embodiment corresponding to the third embodiment but without groove.

FIG. 10 shows a simplified variant of this third embodiment whereby the only difference is that this simplified embodiment has no circumferential groove 8 so that the user guides the treatment device along the forward nail edge either with the mantle surface 18 or the end face 19 without the nail being received in a groove.

Figure 5A:
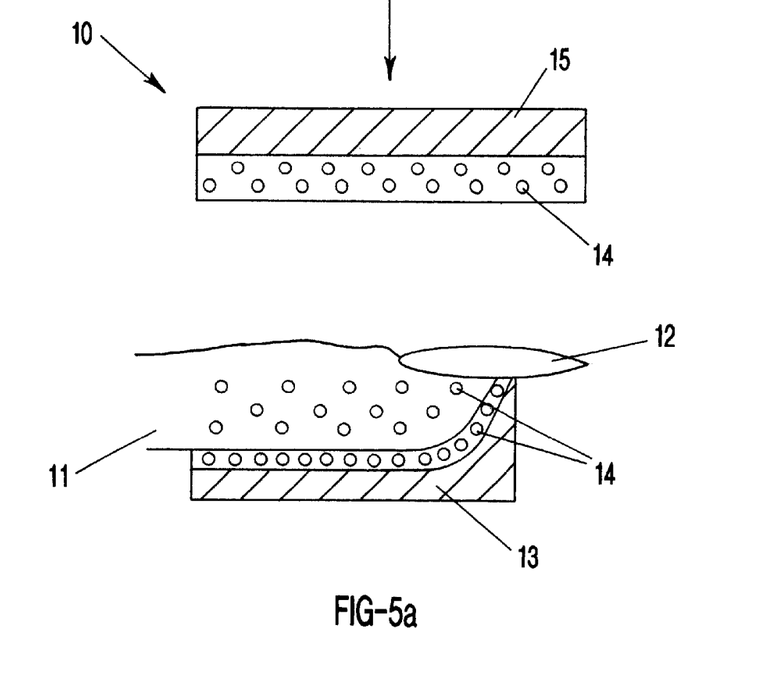
FIGS. 5a and b a protective finger holder for the finger to be treated.
Figure 5B:
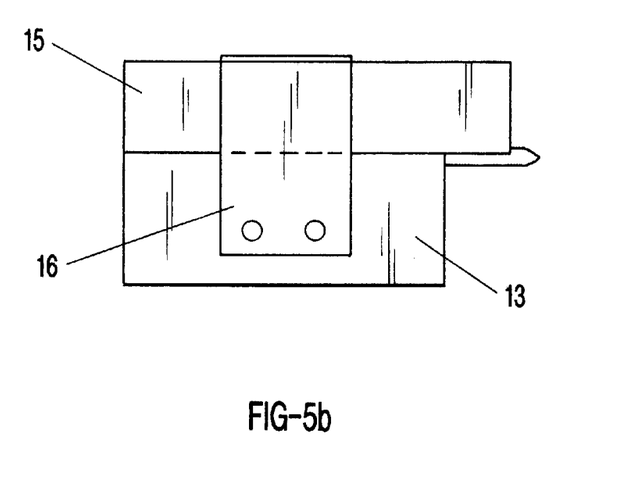
Figure 6A:
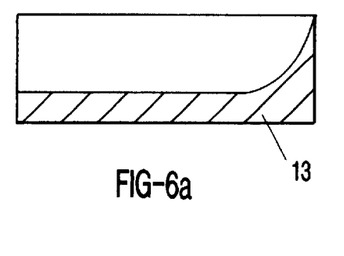
FIGS. 6a–c the bottom part of the protective finger holder in FIGS. 5a and b.
Figure 6B:
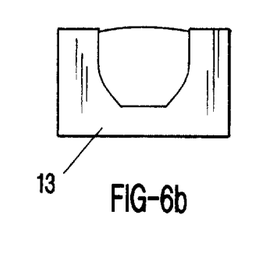
Figure 6C:
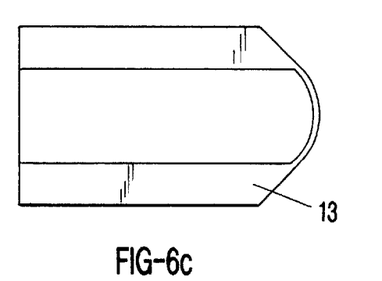
Figure 7A:
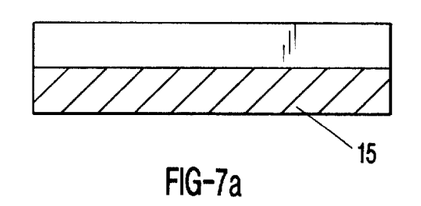
FIGS. 7a–c the top part of the protective finger holder in FIGS. 5a and b.
Figure 7B:
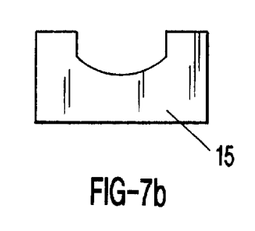
Figure 7C:
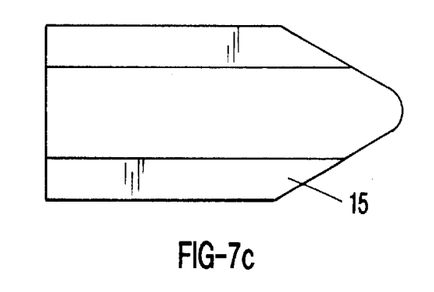

In FIGS. 5a and b a protective finger holder 10 is shown in a schematic longitudinal sectional view (FIG. 5a) as well as in a side view in the operational state of the protective finger holder 10 (FIG. 5b). The basic idea is that the finger 11 of the person to be treated is secured and cooled within the protective finger holder 10 such that only the forward end of the fingernail 12 is exposed. For this purpose, the protective finger holder 10 has a tub-shaped bottom part 13 (FIGS. 6a to c) into which the finger 11 is inserted. Below the finger 11 moist cotton ball 14 is positioned within the tub and the fingernail 12 projects past the upper edge of the bottom portion 13. Furthermore, the protective finger holder 10 has a top portion 15 which is also tub-shaped and covers the upper side of the finger 11 (FIGS. 7a to c). In FIG. 5a the situation shortly before applying the top portion 15 onto the bottom portion 13 is represented whereby here also a moist cotton ball 14 is arranged between the top portion 15 and the finger 11. FIG. 5 shows schematically how the bottom portion 13 and the top portion 15 are secured by a rubber band 16 (or by a velcro closure) such that only the forward end of the fingernail 12 projects from the protective finger holder 10. By cooling with the moist cotton ball 14 it is prevented that the fingernail 11 and the non-treated areas of the fingernail 12 will be heated.

Figure 8A:
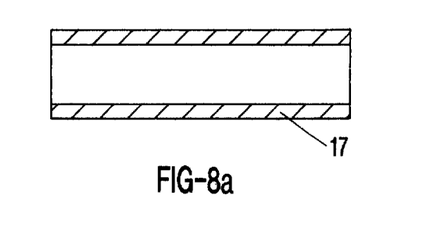
FIGS. 8a and b a cushion filled with cooling liquid for the protective finger holder of FIGS. 5a and b.
Figure 8B:
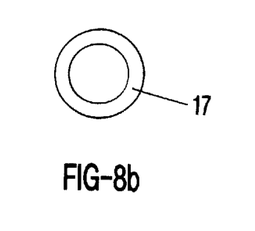

Instead of the cotton ball 14 it is also possible to use a hose-shaped cushion 17 made of plastic material or silicone material which is filled with a cooling liquid. This cushion 17 is slipped onto the finger and subsequently introduced into the protective finger holder 10. This also results in cooling of the finger 11 by the cooling liquid.

Figure 11A:
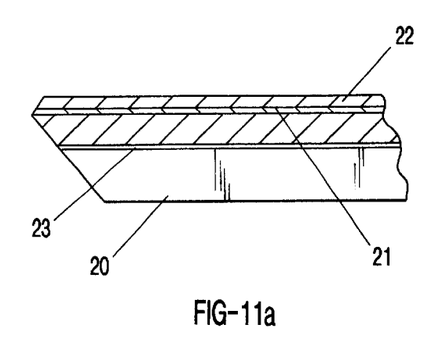
FIGS. 11a–c a fifth embodiment for polishing the nail surface as well as for removing and pushing back the cuticle.
Figure 11B:
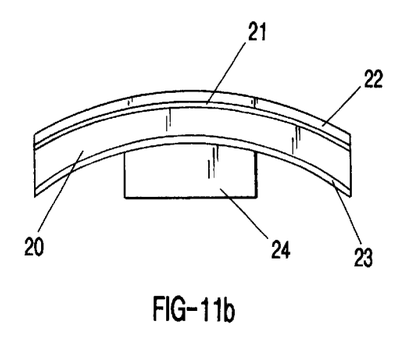
Figure 11C:
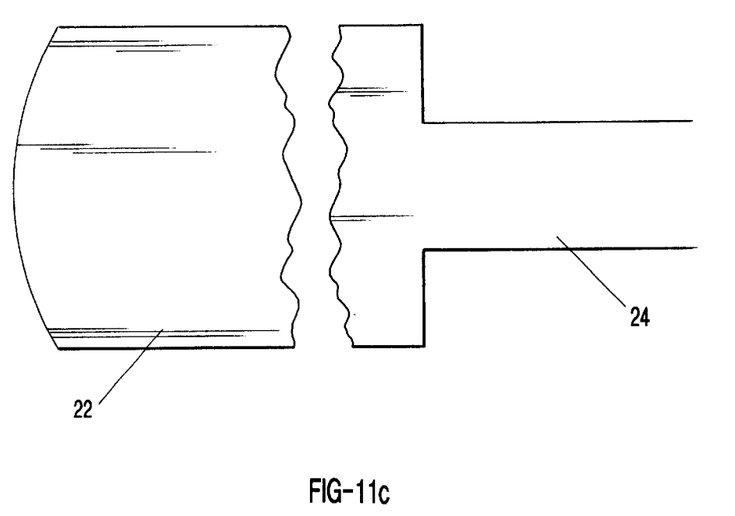

FIGS. 11a to c show the heat treatment device for polishing the nail surface and for removing and pushing back the cuticle. The device is comprised of a curved base body 20. At the upper side a heating foil 21 with temperature sensor is glued or vulcanized thereto. This heating foil 21 is sandwiched between the curved base body 20 and an upper insulation cover 22. At its underside the curved base body 20 has a polishing medium coating 23 which may be polishing paper, a polishing stone or similar material. Instead of the polishing medium coating 23 it is also possible to use a polishing paste or a polishing cream. At the rearward end the device has an attachment 24 to a non-represented holder.

For polishing the nail surface the device is placed onto a nail and moved back and forth. Since the underside of the curved base body 20 is heated, a small portion of the surface of the nail material will melt and become more uniform in the sense of a polishing effect. With a respective movement of the device it is also possible to remove or push back the cuticle at the same time.

Figure 12A:
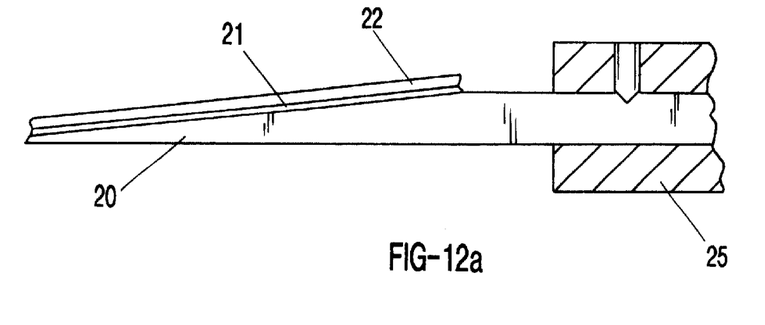
FIGS. 12a–d a sixth embodiment for fusing an artificial fingernail onto a natural fingernail in two alternatives.
Figure 12B:
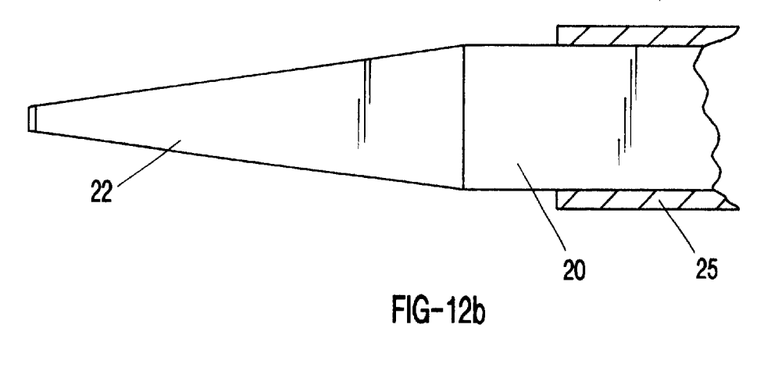
Figure 12C:
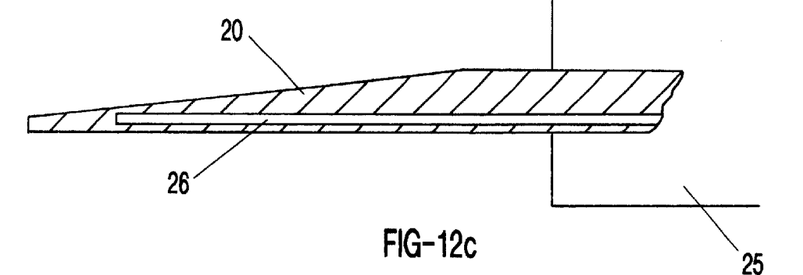
Figure 12D:
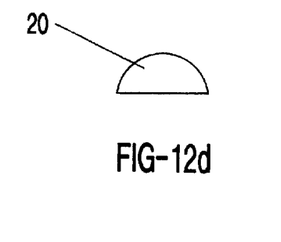
Figure 13A:
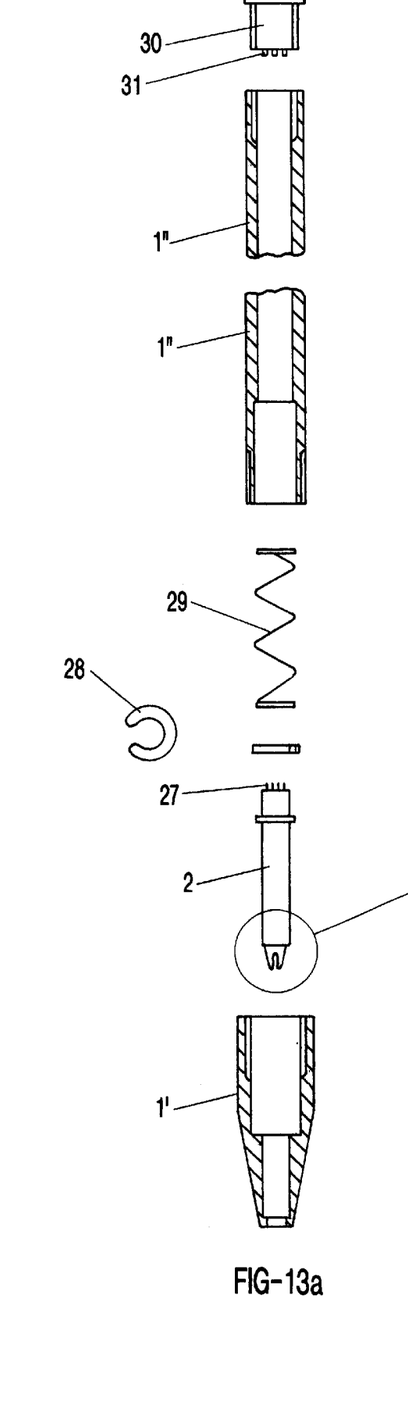
FIGS. 13a–d a schematic sectional view of a last embodiment of a device for treating the forward nail edge of fingernails and toenails in an exploded view.
Figure 13B:
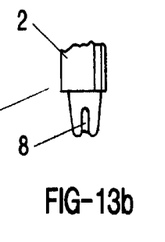
Figure 13C:
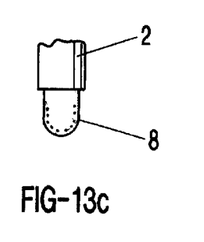
Figure 13D:
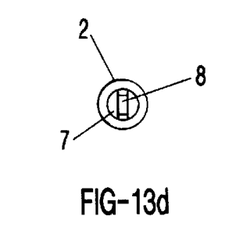

In FIGS. 12a to d a device for fusing an artificial fingernail onto a natural fingernail is represented whereby FIGS. 12a and b shows a first variant and FIGS. 12c and d show a second variant. In the first variant of FIGS. 12a and b, a pointed base body 20 is provided which has a semi-circular cross-sectional profile. The base body 20 is secured to a holder 25. At its upper side the base body 20 has a heating foil 21 with temperature sensor as well as an insulation cover 22. The embodiment according to FIGS. 12c and d differs from the first variant in that instead of the heating foil 21 a heating cartridge 26 is provided.

Finally, FIGS. 13a to d show a further version of a device for treating fingernails and toenails which basically corresponds to the device represented in the first version of FIG. 1. A tubular, pin-shaped holder 1 is provided which is comprised of a sleeve-shaped head portion 1' made of PTFE (Teflon) as well as the actual grip portion 1". The sleeve-shaped head portion 1' serves for receiving a cartridge-shaped heating element 2 to be inserted into the head portion 1". As can be seen in the individual representations of FIGS. 13b to d, the end face 7 of this heating element 2 has a groove 8. At the rear of the cartridge-shaped heating element 2 connectors 27 for an electric voltage supply are provided.

During assembly, a washer 28 is placed onto the heating element 2 inserted into the head portion 1' and furthermore a spiral pressure spring 29. Finally, the grip portion 1" is screwed onto the head portion 1' and thus secures the heating element, whereby the pressure spring 29 is supported at a corresponding projection in the interior of the grip portion 1" and pushes the heating element 2 into the forward position within the head portion 1'. The rearward end of the grip portion 1" is closed off by threading a so-called cap thereon. This cap 30 includes also connectors 31 in the form of soldered pins for the electrical connections.

For operating the treatment device the heating element 2 is heated by a respective resistance heating device via the electric connector so that the head of the heating element 2 with the groove 8 is heated.

The present invention is, of course, in no way restricted to the specific disclosure of the specification and drawings, but also encompasses any modifications within the scope of the appended claims.

What is claimed is:

1. A device for treating natural fingernails and toenails and artificial fingernails and toenails, said device comprising:
   a heating unit for heating a fingernail or toenail to a temperature at which the material of the fingernail or toenail begins to melt, said device adapted to be guided along a leading edge of the fingernail and toenail, thereby melting said leading edge.

2. A device according to claim 1, wherein said heating unit is guided along a leading edge of the fingernail and toenail.

3. A device according to claim 2, wherein said heating unit is rod-shaped and has a curved mantle surface and an end face, wherein said curved mantle surface or said end face of said heating unit is guided along the leading edge of the fingernail or toenail.

4. A device according to claim 3, wherein said heating unit has a slot-shaped groove for receiving the leading edge of the fingernail or toenail.

5. A device according to claim 4, wherein said slot-shaped groove is provided at an end face of said heating unit, wherein said end face and said slot-shaped groove have a matching planar or a matching curved shape.

6. A device according to claim 3, wherein said mantle surface is cylindrical and wherein said groove extends over the entire circumference of said cylindrical mantle surface.

7. A device according to claim 1, wherein said heating unit is slidable along a surface of the fingernail or toenail for polishing the surface.

8. A device according to claim 7, wherein said heating unit is curved.

9. A device according to claim 7, wherein said heating unit comprises a layer of polishing medium on a contact side of said heating unit contacting the fingernail or toenail.

10. A device according to claim 3, wherein said heating unit is curved and pressed onto an artificial fingernail for attaching an artificial fingernail to a natural fingernail.

11. A device according to claim 3, wherein said heating unit is a heat storage device having an external heat source in the manner of a furnace.

12. A device according to claim 1, comprising a control for controlling the temperature of said heating device.

13. A device according to claim 1, comprising a holder, wherein said heating unit comprises heating element arranged at said holder.

14. A device according to claim 1, comprising a covering device for covering, cooling, or covering and cooling of portions of the fingernail or toenail not to be treated.

* * * * *